United States Patent
Cosimbescu

(12)
(10) Patent No.: US 6,664,396 B1
(45) Date of Patent: Dec. 16, 2003

(54) ONE STEP SYNTHESIS FOR QUINACRIDONE COMPOUNDS

(75) Inventor: Lelia Cosimbescu, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/373,246

(22) Filed: Feb. 24, 2003

Related U.S. Application Data

(60) Provisional application No. 60/392,089, filed on Jun. 27, 2002.

(51) Int. Cl.$^7$ .............................................. C07D 471/04
(52) U.S. Cl. .............................. 546/41; 546/49; 546/56; 546/57
(58) Field of Search .............................. 546/41, 49, 56, 546/57

(56) References Cited

U.S. PATENT DOCUMENTS 6,376,107 B1    4/2002   Heuer et al.

OTHER PUBLICATIONS

H. Bruce Goodbrand, et al, "Ligand–Accelerated Catalysis of the Ullmann Condensation: Application to Hole Conducting Triarylamines", J. Org. Chem. 1999, 64, pp. 670–674.

Elizabeth Buck, et al, "Ullmann Diaryl Ether Synthesis: Rate Acceleration by 2,2,6,6–Tetramethylheptane–3,5–dione", Organic Letters, vol. 4, No. 9, 2002, pp. 1623–1626.

SciFinder Version 2001 for CS 262587.

SciFinder Version 2001 for CS 268491.

Primary Examiner—Patricia L. Morris
(74) Attorney, Agent, or Firm—Arthur E. Kluegel

(57) ABSTRACT

Disclosed is a process for forming a N,N'-diarylquinacridone compound comprising the step of reacting a N,N'-unsubstituted quinacridone compound with a haloaryl compound in the presence of a metal or metal compound to arylate the N and N' positions and form the corresponding N,N'-diarylquinacridone compound. The process is versatile and provides high yields and purity for the synthesis of N,N'-diarylquinacridone compounds.

38 Claims, No Drawings

ONE STEP SYNTHESIS FOR QUINACRIDONE COMPOUNDS

CROSS-REFERENCE TO RELATED APPLICATION

This application claims the benefit of U.S. Provisional Application No. 60/392,089 filed Jun. 27, 2002.

FIELD OF THE INVENTION

This invention relates to the field of organic synthesis and to a process for forming a N,N'-diarylquinacridone compound comprising the step of reacting a N,N'-unsubstituted quinacridone compound with a haloaryl compound in the presence of a metal to arylate the N and N' positions and form the corresponding N,N'-diarylquinacridone compound.

BACKGROUND OF THE INVENTION

N,N'-diarylquinacridones have become useful materials and have necessitated synthetic methods for preparing them. In U.S. Pat. No. 6,376,107, Heuer et al disclose the preparation of N,N'-dialkylquinacridones by contacting unsubstituted quinacridones and alkyl halides with a base such as sodium hydride, in a solvent such as dimethylacetamide or dimethylformamide. This is however not extended to the case of aryl halides.

According to Sci Finder, Radl et al, in a series of disclosures (Czech patents 262587 and 261338), disclose the reaction of 4-oxodihydroquinolines (not a quinacridone) with nitroaryl halides with a base such as sodium hydride in a solvent such as dimethylformamide. The disclosure teaches the use of aryl nitrohalides.

Song et al (*Org. Letters*, 2002, 4, 1623–1626) have shown a reaction in the presence of cuprous chloride and a dione to form diaryl ethers. They did not extend this reaction to nitrogen compounds such as quinacridones. Goodbrand et al (J. Org. Chem., 1999, 64, 670–674) have shown that Ullman condensation can be accelerated in the presence of a ligand; this was applied to the synthesis of simple triaryl amines, not to deactivated amines, such as quinacridones.

It is a problem to be solved to provide a process for the synthesis of N,N'-diarylacridone compounds that is simple and efficient.

SUMMARY OF THE INVENTION

The invention provides a process for forming a N,N'-diarylquinacridone compound comprising the step of reacting a N,N'-unsubstituted quinacridone compound with a haloaryl compound in the presence of a metal to arylate the N and N' positions and form the corresponding N,N'-diarylquinacridone compound. The process is simple and efficient.

DETAILED DESCRIPTION OF THE INVENTION

The invention process is summarized above. The process is useful for synthesizing N,N' aryl quinacridone compounds by a simplified process of reacting an N,N'-unsubstituted quinacridone compound with a haloaryl compound to arylate the N and N' positions. The phrase "N,N'-unsubstituted" means that neither of the nitrogen atoms of the quinacridone are substituted.

The N,N'-unsubstituted quinacridone compound may be usefully represented by Formula 1:

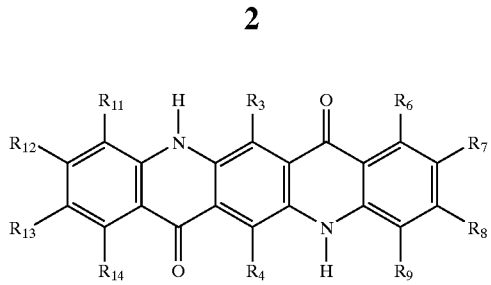

where $R_3$ and $R_4$ can be hydrogen, alkyl, aryl, alkoxy, fluorine, chlorine, nitro or cyano groups; $R_6$–$R_{14}$ can be hydrogen, or halogen such as chlorine or fluorine, nitro, cyano, carboxyl, or groups which may be further substituted such as alkyl including branched or straight chain, such as methyl, trifluoromethyl, ethyl, alkoxy such as methoxy, ethoxy, propoxy, aryl such as phenyl, 2,4,6, trimethylphenyl, naphthyl, biphenyl, aryloxy such as phenoxy, tolyloxy, carbonamido such as acetamido, benzamido, acyl such as acetyl, phenoxycarbonyl, sulfonyl such as methylsulfonyl, phenoxysulfonyl, acyloxy such as acetyloxy, benzoyloxy, N-substituted carbamoyl, N-substituted sulfamoyl, a heterocyclic oxy group or a heterocyclic thio group; and the heterocyclic nitrogen atoms of 1 have no substituents other than hydrogen atoms. When a molecule may have two or more substituents, the substituents may join together to form a ring, such as a fused ring, unless otherwise provided. Conveniently, $R_3$ and $R_4$ may be hydrogen, fluorine, chlorine, methyl, ethyl, propyl, methoxy, ethoxy, phenyl, and $R_6$–$R_{14}$ may be the same as $R_3$ and $R_4$ plus nitro, trifluoromethyl, cyclohexyl, or cyano groups. One or more of $R_6$ and $R_7$ or $R_8$ and $R_7$ or $R_8$ and $R_9$, or $R_{12}$ and $R_{13}$ or $R_{11}$ and $R_{12}$ or $R_{13}$ and $R_{14}$ can form a fused ring such as a benzene ring, a cyclohexyl ring, or a benzoxazole ring. Desirably, the substituents adjacent to the nitrogen reaction site are hydrogen, or at least one of $R_4$ and $R_9$, and at least one of $R_{11}$ and $R_3$ is hydrogen.

The haloaryl compound is conveniently a halophenyl compound represented by formula 2:

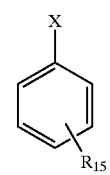

In Formula 2, X represents a halogen atom. Formula 2 is suitably a bromoaryl or iodoaryl compound, and desirably an iodoaryl compound; that is, X is suitably iodine or bromine, and desirably iodine. $R_{15}$ represents hydrogen or one or more substituent groups on the phenyl ring, desirably a substituents having a Hammet's σ constant at least 0.05 or more positive than the corresponding methyl group (in the same position). Each $R_{15}$ may independently be hydrogen or may be selected by those skilled in the art to attain the desired properties for a specific application and can include the same substituents broadly described above for $R_6$–$R_{14}$. Conveniently, $R_{15}$ can be hydrogen, fluorine, chlorine, methyl, ethyl, propyl, methoxy, ethoxy, phenyl, nitro, trifluoromethyl, cyclohexyl, cyano. Two $R_{15}$ groups can be joined to form a fused ring with the parent benzene ring.

Suitably, $R_{15}$ can be hydrogen, methyl, ethyl, cyclohexyl, hydroxy, phenyl, methoxy, or ethoxy. Bulky substituents ortho to the halogen are not convenient and it is desirable that at least one of the ortho positions to the halogen be hydrogen.

The amount of the haloaryl compound used, relative to the starting quinacridone as per formula 1, can range from 2–12 equivalents. The resulting product of this process will be an N,N'-diarylquinacridone compound, represented by N,N'-diphenylquinacridone compound 3.

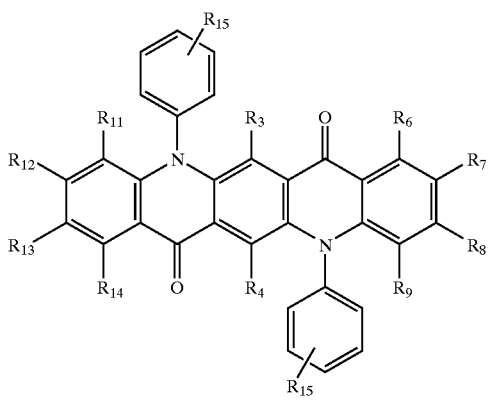

3

The reaction occurs in the presence of a base. More specifically, the base needed to perform the process is a dissociative base. The term dissociative base herein refers to alkaline substances known in the art to dissociate in certain solvents, and particularly in polar solvents, into discrete cations and anions. Such dissociative bases include, for example, sodium carbonate, trisodium phosphate, alkali metal alkoxides such as sodium tert-butoxide, alkali metal hydroxides such as sodium hydroxide, alkali metal hydrides such as sodium hydride, and tetrabutylammonium ethoxide. Conveniently the base used can be $K_2CO_3$, $Cs_2CO_3$, sodium tert-butoxide, or sodium hydride suitably in the amount of 2–3 equivalents per quinacridone mole.

The metal used to effect the coupling can be in the metallic form, a metal compound, or a mixture thereof. The metal is conveniently a transition metal. In the metallic form, and typically, the metal can be chosen from copper (Cu) and palladium (Pd). For a metal compound, particularly suitable are certain compounds of copper and palladium. Examples of copper compounds effective for this are. copper (I) iodide, copper(I) chloride, and copper(I) oxide, especially copper iodide. The amount of copper compound used can be a molar equivalent or can be in a catalytic quantity, which is herein defined as an amount of 2 mole % to 5 mole % relative to 1. A mixture of a copper compound and copper metal is desireable. In such a case, the amount of copper metal can be in the range of 1 equivalent to 5 mole % relative to 1. Palladium compounds effective for this coupling can include palladium diacetate, tris(dibenzylidine acetone) dipalladium, bis(triphenylphosphine)palladium dichloride, or tetrakis(triphenylphosphine)palladium. The amount of palladium compound used can be a molar equivalent or desireably can be in a catalytic quantity, which is herein defined as an amount of 2 mole % to 20 mole % relative to 1.

In addition to the above metal compounds, the use of certain ligands can enhance the effectiveness of this reaction by lowering the activation energy level of the reaction by comlexing the metal or metal compound. Such ligands include but are not limited to 1, 10-phenanthroline, 1,2-trans-cyclohexyldiamine, tri(tert-butyl)phosphine, tricyclohexylphosphine, triphenylphosphine, beta-keto carbonyl compounds including dialkyl beta-keto carbonyl compounds and particularly di-tert-butyl beta-keto carbonyl compounds such as 2,2,6,6-tetramethylheptane-3,5-dione, imidazolium ligands, 2-dicyclohexylphosphinobiphenyl, and 2-dicyclohexylphosphino-2'-(N,N-dimethylamino) biphenyl. The appropriate combination of ligand and a particular metal catalyst can be readily determined by those skilled in the art.

This procedure is conveniently carried out in a solvent. Particularly effective solvents are aprotic solvents, including but not limited to, tetrahydrofuran, toluene, xylene, dioxane, dimethylformamide, dimethyl acetamide, N-methylpyrrolidone, and dichlorobenzene. The choice of solvent is dictated by the solubility of the starting material (N,N'-unsubstituted quinacridone compound 1) and by the temperature required to effect the transformation. Under certain conditions, the reaction can be conducted without an added solvent, but wherein an excess of 2 can serve the function of a solvent.

Under the reaction conditions stated above, the temperature needed to effect the coupling is typically room temperature (20° C.) or higher. Conveniently, the reaction can be carried out at higher temperatures with temperatures of at least 1 40° C. conveniently employed. The temperature requirements can also be dictated by the nature of the substituents described in Formulas 1 and 2, and thus the solubility of the starting material.

The scheme of the invention is exemplified in the following, to prepare N,N'-diphenylquinacridone:

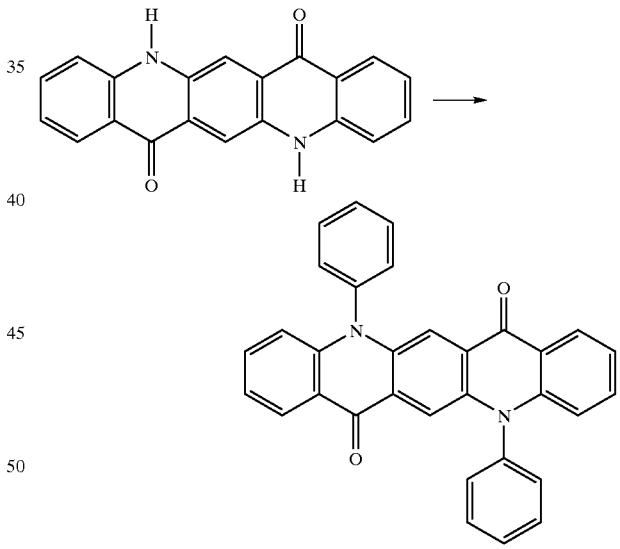

The resulting N,N'-diarylquinacridone is typically employed by incorporation into a light emitting layer of an OLED device, e.g. as a dopant. As more fully described in U.S. Pat. Nos. 4,769,292 and 5,935,721, the light-emitting layer (LEL) of an organic EL element includes a luminescent or fluorescent material where electroluminescence is produced as a result of electron-hole pair recombination in this region. The light-emitting layer comprises a single material, but more commonly comprises a host material doped with a guest compound or compounds where light emission comes primarily from the dopant and can be of any color. The host materials in the light-emitting layer can be an electron-transporting material, a hole-transporting material, or another material or combination of materials that support hole-electron recombination. Dopants are typically coated as 0.01 to 10% by weight into the host material. Polymeric materials such as polyfluorenes and polyvinylarylenes (e.g., poly(p-phenylenevinylene), PPV) can also be used as the host material. In this case, small molecule dopants like 3 can be molecularly dispersed into the polymeric host, or the dopant could be added by copolymerizing a minor constituent into the host polymer.

An important relationship for choosing a dopant is a comparison of the bandgap potential which is defined as the energy difference between the highest occupied molecular orbital and the lowest unoccupied molecular orbital of the molecule. For efficient energy transfer from the host to the dopant molecule, a necessary condition is that the band gap of the dopant is smaller than that of the host material.

Host and emitting molecules known to be of use include, but are not limited to, those disclosed in U.S. Pat. No. 4,768,292, U.S. 5,141,671, U.S. Pat. No. 5,150,006, U.S. Pat. No. 5,151,629, U.S. Pat. No. 5,405,709, U.S. Pat. No. 5,484,922, U.S. Pat. No. 5,593,788, U.S. Pat. No. 5,645,948, U.S. Pat. No. 5,683,823, U.S. Pat. No. 5,755,999, U.S. Pat. No. 5,928,802, U.S. Pat. No. 5,935,720, U.S. Pat. No. 5,935,721, and U.S. Pat. No. 6,020,078.

When used as a light emitting dopant, the N,N'-diarylquinacridone compound can be unsubstituted or optionally contains on the two aryl groups and the quinacridone nucleus only substituent groups having Hammett's σ constant values at least 0.05 more positive than that for a corresponding methyl group. Such substituent groups can include up to two substituent groups directly on the carbon members of the quinacridone nucleus, provided that said substituent groups do not form a ring fused to the five-ring quinacridone nucleus. In such a case, N,N'-unsubstituted quinacridone compound 1 and haloaryl compound 2 are unsubstituted or substituted only with groups having a Hammett's σ constant at least 0.05 more positive than the corresponding methyl group. The Hammett's constant measures the relative electron withdrawing ability of a substituent on an aryl ring with more positive values being more electron withdrawing. Values are given in numerous handbooks such as *Substituent Constants for Correlation Analysis in Chemistry and Biology*, C. Hansch and A. J. Leo, Wiley, New York (1979) and *pKa Prediction for Organic Acids and Bases*, D. D. Perrin, B. Dempsey, and E. P. Serjeant, Chapman and Hall, New York (1981). Most groups other than alkyl, alkoxy, hydroxy and amine groups satisfy this requirement and are thus permissible substituents, e.g. halogen, aryl, aromatic heterocycle, and fused aromatic or hetercyclic rings. The aryl group substituent can be e.g. phenyl, biphenyl, and naphthyl. Unsubstituted N,N'-diarylquinacridone is a compound useful in the invention. Conveniently used are dopants where the diaryl groups are diphenyl groups.

When substituent groups are employed, they can suitably include up to two substituent groups on the carbon members of the quinacridone nucleus. Greater numbers do not provide further advantages, are more complicated to synthesize, and tend to adversely affect color.

Unless otherwise specifically stated, use of the term "substituted" or "substituent" means any group or atom other than hydrogen. Unless otherwise provided, when a group, compound or formula containing a substitutable hydrogen is referred to, it is also intended to encompass not only the unsubstituted form, but also form further substituted with any substituent group or groups as herein mentioned, so long as the substituent does not destroy properties necessary for device utility. Suitably, a substituent group may be halogen or may be bonded to the remainder of the molecule by an atom of carbon, silicon, oxygen, nitrogen, phosphorous, sulfur, selenium, or boron. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen, sulfur, phosphorous, or boron. such as 2-furyl, 2-thienyl, 2-benzimidazolyloxy or 2-benzothiazolyl; quaternary ammonium, such as triethylammonium; quaternary phosphonium, such as triphenylphosphonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, electron-withdrawing groups, electron-donating groups, and steric groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

EXAMPLES

Table 1 illustrates a few examples of reaction conditions employed in preparing N,N-diphenylquinacridone (DPQA) from unsubstituted quinacridone and iodobenzene and the resulting yields. The yields are based on quinacridone starting material.

a catalytic amount of 2,2,6,6-tetramethyl-3,5-heptanedione (60 mg, 20 mol %) was added as a ligand for the copper. The reaction mixture was stirred at 150° C. for 1 day, after which it was allowed to cool to room temperature and a fresh portion of the diketone (60 mg, 20 mol %) was added, along with another equivalent of NaH (60 mg, 1 eq). The reaction mixture was brought back up to 150–160° C. and stirred for another day. The additional base and di-ketone increased the amount of product by about 5–10%, as estimated by TLC. When the reaction mixture was cooled to room temperature, about 30 mL of methylene chloride were added and the heterogeneous mixture stirred for 10–15 minutes. The solids (inorganic salts and unreacted quinacridone) were filtered off and the mother liquor was left standing for 2–3 h, until more material precipitated out; the precipitate was mostly unreacted quinacridone. The precipitate was removed by filtration. The filtrate was concentrated to about 20 mL and then passed through a silica gel column using $CH_2Cl_2$ as the eluting solvent. The isolated DPQA (0.40 g) also included, as illustrated by TLC, a non-polar impurity and very little starting material. The crude material was sublimed at 350 ° C. The non-polar impurity was retained in the boat, while the little residual starting material sublimed together with the product, to obtain 0.31 g (0.67 mmole, 42%) of almost pure DPQA. Another run of this reaction gave about a 30% yield.

Example Inv-2

Example Inv-2 uses the same conditions as Example Inv-1, with the exception that the reaction was run in the presence of 50 mL of N-methylpyrrolidinone (NMP). The quinacridone (0.5 g, 1 .58 mmol, 1 eq) was combined together with sodium hydride (0.16 g, 3.6 mmol, 2.5 eq), under nitrogen, in a 100 ml flask. The N-methyl pyrrolidone was added (50 ml) followed by the addition of copper (0.1 g, 1.58 mmol, 1 eq) and copper(I)iodide (60 mg, 20 mol %), in one portion. The diketone catalyst was added last (60 mg, 20 mol %). The resulting mixture was heated to 140–150° C. When the mixture reached the target temperature, an addi-

TABLE 1

Illustrative Examples

| Example | Type | Conditions | Base | Temp | Ligand | Yield |
|---|---|---|---|---|---|---|
| Inv-1 | Inventive | Cu (1 eq), CuI (15%), iodobenzene (3 mL), neat | NaH | 160 C. | 2,2,6,6-tetramethyl-3,5-heptanedione | 30, 42% |
| Inv-2 | Inventive | Cu (1 eq), CuI (20%), iodobenzene (2 mL), NMP (50 mL total vol) | NaH | 160 C. | 2,2,6,6-tetramethyl-3,5-heptanedione | 20% |
| Inv-3 | Inventive | Cu (1 eq), CuI (20%), iodobenzene (3 mL), neat | NaOtBu | 140–150 C. | 1,10-phenanthroline | 13% |
| Inv-4 | Inventive | Cu (1 eq), CuI (20%), iodobenzene (3 mL), neat | $Cs_2CO_3$ | 140–150 C. | 1,10-phenanthroline | 10% |
| Comp-1 | Comparative | Cu (1 eq), CuI (20%), iodobenzene (2.5 eq), NMP (50 mL total vol) | $K_2CO_3$ | RT | none | no rxn |
| Comp-2 | Comparative | triphenylbismuth diacetate (2.1 eq), $CCl_4$, (50 mL total vol) | N/A | 80 C. | N/A | no rxn |

Example Inv-1

Preparation of N,N-diphenylquinacridone: A 50 mL dry round bottom flask was charged with quinacridone (0.5 g, 1.58 mmol, 1 eq), copper (0.1 g, 1.58 mmol, 1 eq) and copper(I) iodide (45 mg, 15 mol %). Then iodobenzene (3 mL, about 11 eq) was added followed by sodium hydride (0.19 g, 4.74 mmol, 3 eq). To the dark-blue resulting mixture tion funnel was affixed to the flask, and a solution of iodobenzene was added dropwise (2.5 mL, 12 eq, in 20 mL of NMP). The reaction mixture was stirred overnight at 150–160° C. The mixture was allowed to cool at room temperature, about 30 mL of $CH_2C_{12}$ were added and the mixture chilled in ice. While still cold, the inorganic salts together with most of the quinacridone starting material were removed by filtration. The very dark brown-purple filtrate included both starting material and DPQA product in a ratio of about 3:1/DPQA:quinacridone, as estimated by TLC (9:1/$CH_2Cl_2$:EtOAc). The filtrate was chilled until more starting material precipitated out; again all the solids were removed by filtration. The mother liquor was concentrated down and the resulting NMP solution of DPQA was added to a vigorously stirred ice water. The product precipitated out and it was isolated by filtration. The solid cake was washed with water, followed by 5 mL of methanol to dry. The isolated solid (0.14 g, 20%) had very little starting material present, as determined by TLC.

Example Inv-3

Example Inv-3 uses the same conditions as Example Inv-1, with the exception that the ligand used is 1,1 0-phenanthroline, and the base is NaOtBu. The quinacridone (0.5 g, 1.58 mmol, 1 eq), copper (0.10 g, 1.58 mmol, 1 eq) and copper(I)iodide (60 mg, 20 mol %) were added to a 50 mL round bottom flask. Then sodium tert-butoxide (0.38 g, 3.95 mmol, 2.5 eq) and the 1,1 0-phenanthroline (60 mg, 20 mol %) were added, followed by 3 mL of iodobenzene (excess, about 11 eq). The temperature was raised to 140–150° C. and the mixture stirred overnight. The reaction mixture was then cooled down, about 40 mL of $CH_2Cl_2$ were added and the resulting suspension stirred for 15 minutes. The inorganic solids together with any quinacridone starting material were filtered off (very little product was retained on the filter cake), the filter cake washed with $CH_2Cl_2$ (10 mL), and the mother liquor was chilled, until more material precipitated off. Once again the solids were removed by filtration. The resulting mother liquor was concentrated to a thick syrup and the product was precipitated out by adding heptane (about 150 mL) with vigorous stirring. The suspension was chilled in ice and the product was isolated by filtration, to yield 0.10 g (13%) of a rust color solid.

Example Inv-4

Example Inv-4 uses the same conditions as Example Inv-3, with the exception that the base used was $Cs_2CO_3$. A 50 mL flask was charged with quinacridone (0.5 g, 1.59 mmol, 1 eq), copper (104 mg, 1.59 mmol, 1 eq), copper(I) iodide (60 mg, 20 mol %), and $Cs_2CO_3$ (1.29 g, 3.98 mmol, 2.5 eq), followed by the addition of 3 mL of iodobenzene (about 11 eq, excess). The resulting mixture was stirred 140–150° C. for 2 days. About 50 mL of methylene chloride were added to the cooled reaction mixture, and the inorganic solids and most of the starting material were isolated by filtration. The mother liquor was concentrated to a volume of about 25 mL and it was passed through a silica gel plug to remove the starting material ($CH_2Cl_2$:EtOAc/95:5). The fractions containing only the starting material were concentrated to yield only about 5% of product; however most of the other fractions included product as well, and by TLC it was estimated to total another 5–10% additional product.

Example-Comp 1

The quinacridone (0.5 g, 1.58 mmol, 1 eq), copper (0.10 g, 1.58 mmol, 1 eq), copper(I)iodide (60 mg, 20 mol %), $K_2CO_3$ (0.43 g, 3.16 mmol, 2 eq) and iodobenzene (1 mL, 5.6 eq) were combined in a 250 mL flask, together with 100 mL of N-methyl pyrrolidone. The reaction was stirred at room temperature for 1 day. The reaction yielded no product, as indicated by TLC.

Example-Comp 2

The quinacridone starting material (0.20 g, 0.63 mmol, 1 eq), copper (21 mg, 0.32 mmol, 0.5 eq) and triphenylbismuth diacetate (0.774 g, 1.33 mmol, 2.1 eq) were combined in a 250 mL round bottom flask. Carbontetrachloride (90 mL) were added and the resulting suspension was heated to reflux and stirred for 4 h. The progression of the reaction was checked by TLC, and when no product was detected, NMP was added as a co-solvent to help solubility. The resulting mixture was heated to reflux overnight. TLC indicated that the desired product was not obtained.

Several attempts were made to obtain the desired product using palladium but the conditions and materials selected were not effective and it is expected that the correct selection of conditions and materials would provide the desired results.

The results show that, for the inventive samples tested, the yields ranged from 10–42%, while the comparative examples failed to produce any measurable product. Variations in the amounts of metal, solvent, base, and temperature appeared to have an effect on yields. Use of phenylating agents other than haloaryl agents, such as triphenylbismuth, did not result in the formation of any product (Example Comp-2). When iodobenzene was used as the arylating agent, in almost equivalent amounts, and the reaction was run at room temperature (Example Comp-1), with a very mild base, again no product was formed. It appears that temperature helps to solubilize the starting material and to promote the reaction. The use of a ligand, especially 2,2,6, 6-tetramethyl-3,5-haptanedione, coupled with a relatively high temperature (140–160° C.) yielded the most product (Example Inv-1 and Inv-2). An excess of iodobenzene and a high concentration of reactants appears to facilitate the reaction.

The entire contents of the patents and other publications referred to in this specification are incorporated herein by reference. The invention has been described in detail with particular reference to certain preferred embodiments thereof, but it will be understood that variations and modifications can be effected within the scope of the invention.

What is claimed is:

1. A process for forming a N,N'-diarylquinacridone compound comprising the step of reacting a N,N'-unsubstituted quinacridone compound with a haloaryl compound in the presence of a metal or metal compound to arylate the N and N' positions and form the corresponding N,N'-diarylquinacridone compound.

2. The process of claim 1 wherein the metal or metal compound comprises a transition metal.

3. The process of claim 1 wherein the metal or metal compound comprises copper or palladium.

4. The process of claim 3 wherein the metal or metal compound comprises copper.

5. The process of claim 1 wherein the metal is a metal compound selected form the group consisting of CuI, CuCl, $Cu_2O$, palladium diacetate, tris(dibenzylidine acetone) dipalladium, bis(triphenylphosphine) palladium dichloride, and tetrakis(triphenylphosphine)palladium.

6. The process of claim 5 wherein the metal compound comprises CuI.

7. The process of claim 1 wherein the reaction is conducted without an added solvent.

8. The process of claim 1 wherein the reaction is conducted in the presence of an aprotic solvent.

9. The process of claim 1 wherein the solvent is selected from toluene, xylene, dioxane, dimethylformamide, dimethyl acetamide, N-methylpyrrolidone, and dichlorobenzene.

10. The process of claim 1 wherein the haloaryl compound is a bromoaryl or an iodoaryl compound.

11. The process of claim 1 wherein the haloaryl compound is an iodoaryl compound.

12. The process of claim 1 wherein the reaction occurs in the presence of a base.

13. The process of claim 12 wherein the base is a dissociative base.

14. The process of claim 12 wherein the base is a carbonate or a phosphate.

15. The process of claim 12 wherein the base is an alkali metal hydride, an alkali metal hydroxide, or an alkali metal alkoxide.

16. The process of claim 1 wherein the reaction occurs in the presence of a ligand.

17. The process of claim 16 wherein the ligand is a beta-keto carbonyl compound.

18. The process of claim 17 wherein the ligand is a dialkyl beta-keto carbonyl compound.

19. The process of claim 17 wherein the ligand is a di-tert-butyl beta-keto carbonyl compound.

20. The process of claim 16 wherein the ligand is selected from the group consisting of 2,2,6,6-tetramethylheptane-3,5-dione, 1,10-phenanthroline, 1,2-trans-cyclohexyldiamine, tri(tert-butyl)phosphine, tricyclohexylphosphine, triphenylphosphine, imidazolium ligands, 2-dicyclohexylphosphinobiphenyl, and 2-dicyclohexylphosphino-2'-(N,N-dimethylamino)biphenyl.

21. The process of claim 1 wherein the N,N'-diaryl quinacridone compound is a N,N'-diphenylquinacridone compound.

22. The process of claim 1 wherein the haloaryl compound is not further substituted.

23. The process of claim 1 wherein the haloaryl compound is substituted with a group having a Hammett's σ constant at least 0.05 or more positive than the corresponding methyl group in the same position.

24. The process of claim 23 wherein the substituted group is selected from the group consisting of halogen, aryl, aromatic heterocycle, and fused aromatic or heteroaromatic ring.

25. The process of claim 1 wherein the reaction is performed at a temperature of at least 20° C.

26. The process of claim 1 wherein the reaction is performed at a temperature of at least 140° C.

27. The process of claim 1 wherein the haloaryl compound is a halophenyl compound.

28. The process of claim 1 wherein the N,N'-unsubstituted quinacridone compound benzene ring and the haloaryl compound are unsubstituted or substituted only with groups having a Hammett's σ constant at least 0.05 more positive than the corresponding methyl group.

29. The process of claim 28 wherein the substituted group is selected from the group consisting of halogen, aryl, an aromatic heterocycle, and a fused aromatic or heteroaromatic ring.

30. The process of claim 29 wherein the substituted group is selected from the group consisting of phenyl, biphenyl, and naphthyl groups.

31. A process for forming a N,N'-diarylquinacridone compound comprising the step of reacting a N,N'-unsubstituted quinacridone compound of formula 1 with a haloaryl compound of formula 2 in the presence of a metal or metal compound to arylate the N and N' positions and form the corresponding N,N'-diarylquinacridone compound, wherein formula 1 and formula 2 are as follows:

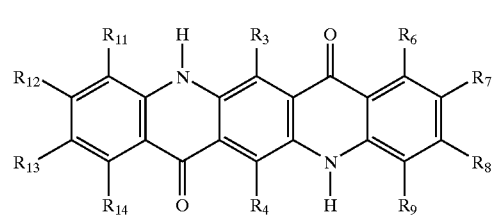

1 wherein $R_3$ and $R_4$ can be hydrogen, alkyl, aryl, alkoxy, fluorine, chlorine, nitro or cyano groups; and $R_6$–$R_{14}$ can be hydrogen, halogen, nitro, cyano, carboxyl, alkyl, alkoxy, aryl, aryloxy, carbonamido, acyl, sulfonyl, acyloxy, a heterocyclic oxy group or a heterocyclic thio group; and

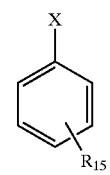

2 wherein X represents a halogen atom and $R_{15}$, may be selected from the same substituents described above for $R_6$–$R_{14}$.

32. The process of claim 31 wherein $R_3$ and $R_4$ may be hydrogen, fluorine, chlorine, methyl, ethyl, propyl, methoxy, ethoxy, phenyl, and $R_6$–$R_{14}$ may be the same as $R_3$ and $R_4$ plus nitro, trifluoromethyl, cyclohexyl, cyano.

33. The process of claim 31 wherein one or more of $R_6$ and $R_7$ or $R_8$ and $R_7$ or $R_8$ and $R_9$, or $R_{12}$ and $R_{13}$ or $R_{11}$ and $R_{12}$ or $R_{13}$ and $R_{14}$ can form a fused benzene ring, a cyclohexyl ring, or a benzoxazole ring.

34. The process of claim 31 wherein the substituents adjacent to the nitrogen reaction site are hydrogen, or at least one of $R_4$ and $R_9$, and at least one of $R_{11}$, and $R_3$ is hydrogen.

35. The process of claim 31 wherein X is iodine or bromine.

36. The process of claim 31 wherein $R_{15}$ can be hydrogen, fluorine, chlorine, methyl, ethyl, propyl, methoxy, ethoxy, phenyl, nitro, trifluoromethyl, cyclohexyl, cyano.

37. The process of claim 31 wherein $R_{15}$ can be a fused ring with the parent benzene ring.

38. The process of claim 31 wherein $R_{15}$ can be hydrogen, methyl, ethyl, cyclohexyl, phenyl, methoxy, or ethoxy.

* * * * *